United States Patent [19]
Hamilton et al.

[11] Patent Number: 4,500,540
[45] Date of Patent: Feb. 19, 1985

[54] THROMBOXANE SYNTHASE INHIBITORS AS INSULIN LOWERING AGENTS AND ANTIOBESITY AGENTS

[75] Inventors: James G. Hamilton, Nutley; Ann C. Sullivan, Cedar Grove; Lawrence D. Tobias, Glen Ridge; Joseph Triscari, Bloomfield, all of N.J.

[73] Assignee: Hoffmann-La Roche Inc., Nutley, N.J.

[21] Appl. No.: 387,721

[22] Filed: Jun. 11, 1982

Related U.S. Application Data

[63] Continuation of Ser. No. 107,484, Dec. 26, 1979, abandoned.

[51] Int. Cl.[3] ................. A61K 31/415; A61K 31/305; A61K 31/44; A61K 31/40

[52] U.S. Cl. .................................... 514/397; 514/398; 514/399; 514/256; 514/381; 514/886; 514/910

[58] Field of Search .......................................... 424/273

[56] References Cited

U.S. PATENT DOCUMENTS

| | | | |
|---|---|---|---|
| 3,637,731 | 1/1972 | Johnson | 260/309 |
| 3,821,415 | 6/1974 | Heyes et al. | 424/273 |
| 3,867,539 | 2/1975 | Henkin | 424/273 |
| 3,880,871 | 4/1975 | Haugwitz et al. | 424/273 |
| 3,991,201 | 11/1976 | Heeres et al. | 424/273 |
| 3,996,366 | 12/1976 | Baker et al. | 424/273 |

FOREIGN PATENT DOCUMENTS

| | | | |
|---|---|---|---|
| 3901 | 5/1979 | European Pat. Off. | |
| 2160017 | 6/1972 | Fed. Rep. of Germany | |
| 2325300 | 12/1973 | Fed. Rep. of Germany | |
| 2227006 | 12/1974 | France | 424/273 |

OTHER PUBLICATIONS

Chem. Abst. 82, 118,787(h) (1975) Aeberli et al.
Chem. Abst. 74, 96456(e) (1971)–Lefebvre et al.
Chem. Abst. 76, 108,708(v) (1972)–Malaisse.
Merck 9th ed. item 4845–1976 Merck & Co.

*Primary Examiner*—Douglas W. Robinson
*Attorney, Agent, or Firm*—Jon S. Saxe; Bernard S. Leon; Matthew Boxer

[57] ABSTRACT

The present disclosure relates to the use of thromboxane synthase inhibitors as antiobesity agents and insulin lowering agents. Such compounds fall into a variety of classes among which are 1-substituted imidazoles, 4-substituted imidazoles, 3-substituted pyridines, 3-substituted indoles, 4-substituted pyrimidines, 5-substituted tetrazoles, pyrazolidines, quinazolines, and substituted xanthene carboxylic acids.

33 Claims, 1 Drawing Figure

THROMBOXANE SYNTHASE INHIBITORS AS INSULIN LOWERING AGENTS AND ANTIONBESITY AGENTS

This is a continuation of application Ser. No. 107,484 filed Dec. 26, 1979, now abandoned.

BACKGROUND OF THE INVENTION

1. Field Of The Invention

Obesity represents a state of increased body fat which may decrease longevity, aggravate the onset and progression of other diseases, e.g., heart disease, diabetes, gallstones, and impace on one's social or economic status. [The Obese Patient, G. A. Bray, Vol. IX in the series "Major Problems in Internal Medicine", W. B. Saunders Co., 1976].

Hyperinsulinemia is a metabolic characteristic of all forms of human and animal obesity. Excess insulin levels not only stimulate food intake and promote lipid biosynthesis and storage, but also reduce lipid mobilization and utilization. Thus, hyperinsulinemia produces and maintains the excess fat deposition which characterizes the obese state. The hyperinsulinemia in obesity appears prior to the development of insulin resistance in tissues and may be due to abnormal regulation of insulin biosynthesis and/or secretion in the pancreas. Thus, the development of agents which reduce insulin levels will have therapeutic importance in the treatment of obesity.

This disclosure relates to the use of thromboxane synthase inhibitors as antiobesity agents and insulin lowering agents.

2. Description Of The Prior Art

A paper entitled "On the Inhibitory Potency of Imidazole and its Derivatives on Thromboxane Synthetase", Hsin-Hsiung Tai et al., Biochemical and Biophysical Research Communications 80: 236–242 (1978) discloses the finding that the relative inhibitory potency of imidazole and derivatives on thromboxane synthase from human platelets is increased by substitution of the 1-position and abolished in other positions. The potency of 1-substituted imidazoles was increased as the side chain became more hydrophobic. Among the imidazole derivatives tested, 1-nonylimidazole and 1-(2-isopropyl phenyl)-imidazole showed the highest potency with $I_{50}$ in the range of $10^{-8}$M. There was no mention, however, of the foregoing thromboxane synthase inhibitors as antiobesity agents or insulin lowering agents.

A paper entitled "Studies on the Thromboxane Synthesizing System in Human Platelet Microsomes", Hsin-Hsiung Tai et al., Biochimica et Biophysica Acta, 531: 286–294 (1978) discloses the use of N-substituted imidazoles, sulfhydryl inhibitors, prostaglandin endoperoxide analog, prostaglandin antagonist and N-0164 as thromboxane synthetase inhibitors. There was, however, no indication that said compounds could be used as antiobesity agents or insulin lowering agents.

An abstract entitled "Metyrapone, An Inhibitor of Thromboxane Synthetase and Platelet Aggregation", Hsin-Hsiung Tai et al., Fed. Proc. 38: 407 (1979), discloses metyrapone(2-methyl-1,2-di-3-pyridyl-1-propanone) as a thromboxane synthase inhibitor. No mention, however, was made of the use of said compound as an antiobesity agent or insulin lowering agent.

An abstract entitled "Synthesis and Biological Properties of Selective Inhibitors of Thromboxane Synthetase", Josef Fried et al., Abstracts, Fourth International Prostaglandin Conference, Washington, D.C., May 27–31, 1979, 37, discloses prostaglandin-like compounds and substances derived by partial synthesis form (+)- and (−)-pinene as thromboxane synthase inhibitors. The prostaglandin-like compounds showed 67% inhibition of thromboxane synthase at 50 μg and the compound derived from pinene showed 50% inhibition at 10 μg. Neither of these compounds, however, disclosed a utility as antiobesity agents or insulin lowering agents.

An abstract entitled "The Effect of SQ 80,338 (1-(3-Phenyl-2-Propenyl)-1H-Imidazole) on Thromboxane Synthetase Activity and Arachidonic Acid-Induced Platelet Aggregation and Bronchoconstriction", D. N. Harris et al., Abstracts, Fourth International Prostaglandin Conference, Washington, D.C., May 27–31, 1979, 46, discloses the use of the aforementioned compound as a thromboxane synthase inhibitor. There was, however, no mention of the aforesaid compound as an antiobesity agent or insulin lowering agent.

An abstract entitled "Inhibition of Dog Platelet Reactivity Following 1-Benzylimidazole Administration", R. H. Harris et al., Abstracts, Fourth International Prostaglandin Conference, Washington, D.C., May 27–31, 1979, 46, discloses the use of the aforementioned compound as a thromboxane synthase inhibitor. There was, however, no mention of said compound as an antiobesity agent or insulin lowering agent.

An abstract entitled "On the Inhibitory Potency of Pyridine and its Derivatives on Thromboxane Synthetase", Hsin-Hsiung Tai et al., Abstracts, Fourth International Prostaglandin Conference, Washington, D.C., May 27–31, 1979, 115, discloses the inhibiting effect of pyridine and its derivatives on microsomal thromboxane synthase activity from human platelets. There was, however, no indication that pyridine or its derivatives could be used as an antiobesity agent or insulin lowering agent.

An abstract entitled "Selective Inhibition of Thromboxane Synthetase by Pyridine and its Derivatives", T. Miyamoto et al., Abstracts, Fourth International Prostaglandin Conference, Washington, D.C., May 27–31, 1979, 82, discloses the inhibition by pyridine of enzymatic formation of $TXB_2$ from $PGH_2$ by rabbit platelet microsomes. There was, however, no mention of pyridine or it derivatives as an antiobesity agent or insulin lowering agent.

European Patent Application No. 0 000 951 discloses pharmaceutical compositions containing a 1-hydrocarbylimidazole as inhibitors of blood platelet aggregation and as antihypertensives. Specific compounds mentioned are 1-methylimidazole, 1-n-butylimidazole, 1-n-pentylimidazole, 1-n-hexylimidazole, 1-pent-2-enylimidazole, 1-pent-4-enylimidazole, 1-(3-methylbutyl)imidazole, 1-cyclohexylmethylimidazole, 1-cycloheptylimidazole and 1-cyclopentylimidazole. There is, however, no mention of any of the foregoing compounds as antiobesity agents or insulin lowering agents.

In accordance with the present invention, it has been found that selected thromboxane synthase inhibitors show a utility as antiobesity agents and insulin lowering agents.

SUMMARY OF THE INVENTION

A method for the treatment of obesity and for the lowering of insulin levels in mammals which comprises administering to the mammal to be treated effective amounts of a thromboxane synthase inhibitor comprising 1-substituted imidazoles, 4-substituted imidazoles, 3-substituted pyridines, 3-substituted indoles, 4-substituted pyrimidines, 5-substituted tetrazoles, pyrazolidines, quinazolines, and substituted xanthene carboxylic acids.

The 1-substituted imidazoles of the present invention have the following formula:

FORMULA I

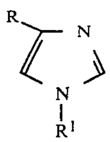

wherein R is H, $NO_2$, or $C_2$–$C_4$ alkenyl; $R^1$ is H, $C_1$–$C_{11}$ alkyl, acyl, aryl, substituted aryl, aralkyl or 3-indolo optionally substituted at the two position by $C_1$–$C_4$ straight or branched chain alkyl.

The 3-substituted pyridines of the present invention have the following formula:

FORMULA II

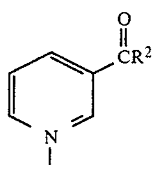

wherein $R^2$ is H, $C_1$–$C_4$ alkyl, aralkyl, 3-indolo optionally substituted at the two position by $C_1$–$C_4$ straight or branched chain alkyl, aryl, substituted aryl, aryl substituted hydrazide.

The 4-substituted pyrimidines of the present invention have the following formula:

FORMULA III

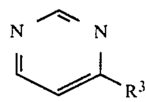

wherein $R^3$ is aryl thioether or aryl pyruvate ester.

The 3-substituted indoles of the present invention have the following formula:

FORMULA IV

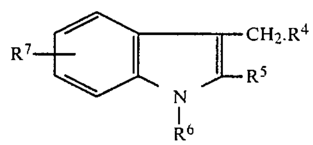

where $R^4$ is $C_1$–$C_4$ straight or branched chain alkyl or COOH, $R^5$ is $C_1$–$C_4$ straight or branched chain alkyl, $R^6$ is substituted aryl or benzoyl, $R^7$ is $C_1$–$C_4$ alkanoyloxy.

Also within the scope of the present invention are 5-substituted tetrazoles as exemplified by 3-(1H-tetrazol-5-yl)-9H-thioxathen-9-one s.s dioxide, pyrazolidines, as exemplified by 1,2-diphenyl-4-[2-[phenyl sufinyl]ethyl]-3,5 pyrazolidinedione; quinazolines as exemplified by 7-methyl-1-(1-methylethyl)-4-phenyl-2(1H)-quinazolinone, and substituted xanthene carboxylic acids as exemplified by 7-(1-methylethoxy)-9-oxo-9H-xanthene-2-carboxylic acid.

DETAILED DESCRIPTION OF THE INVENTION

Figure 1:
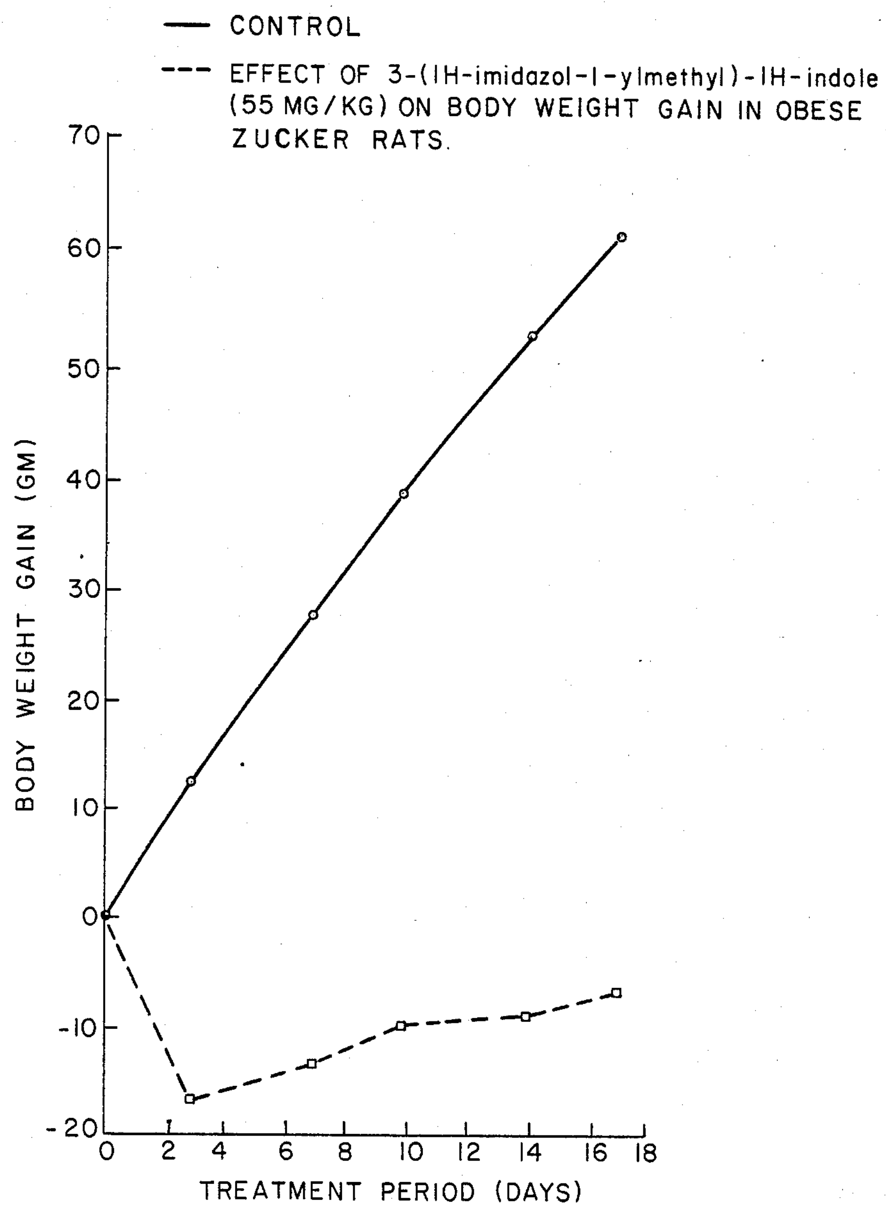
FIG. 1 is a graphic illustration of the weight gain of lean and obese rats treated with one of the thromboxane synthase inhibitors of the present invention compared with the weight gain of control rats who were not treated.

In accordance with the present invention, it has been found that thromboxane synthase inhibitors exhibit insulin-lowering activity as evidenced by in vitro inhibition of insulin release in the isolated perfused rat pancreas. This insulin lowering effect invests thromboxane synthase inhibitors with utility for treating a number of disorders which have, as the basis, elevated insulin levels. For example, elevated insulin levels have been associated in subjects with disease of coronary [N. Peters and C. N. Hales, Lancet, 1: 1144–1145 (1965); E. A. Nikkila et al., Lancet, 2: 508–511 (1965); M. Tzagournis et al., Circulation, 38: 1156–1163 (1968); L. Kashyap et al., Can. Med. Assoc. J., 102: 1165–1169 (1970); C. Malherbe et al., Eur. J. Clin. Invest., 1: 265–270 (1970); and M. M. Gertler et al., Circulation, 46: 103–111 (1972b)], peripheral (T. A. Welborn et al., Lancet, 1: 1336–1337 (1966) and J. M. Sloan et al., Br. Med. J., 4: 586–588 (1970)] and cerebral [M. M. Gertler et al., Geriatrics, 27: 105–120 (1972)] arteries, and insulinoma (a tumor of the insulin-secreting cells of the pancreas), in addition to obesity.

As used herein, alkyl connotes straight or branched chain saturated aliphatic hydrocarbon atoms. Hydroxy means—OH. Alkoxy connotes a straight or branched chain alkyl radical attached to the remainder of the molecule by oxygen (e.g., methoxy,ethoxy, isopropoxy, etc.). Alkenyl means a straight or branched chain unsaturated univalent aliphatic radical. Acyl means an organic radical derived from an organic acid by removal of the hydroxyl group (e.g., acetyl, propionyl, butyryl, etc.). Aryl means an organic radical derived from an aromatic hydrocarbon by the removal of one atom (e.g., phenyl, benzyl, naphthyl, etc.). Substituted aryl means aryl optionally mono or disubstituted by one or more of the following substituents: $C_1$–$C_3$ alkoxy, $C_1$–$C_4$ alkyl, Cl, F, Br, $NO_2$, acyl, or hydroxy. Preferably, the hydroxy substituent is mono substituted in the para position. Aralkyl means arylated alkyl, i.e., a radical in which an alkyl H is substituted by an aryl group. 3 indolo means

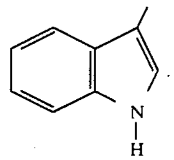

The indole ring may be optionally substituted in the two position by $C_1$–$C_4$ straight or branched chain alkyl. Thioether means an ether group in which the oxygen atom has been replaced by a sulfur atom. Pyruvate ester means an organic salt formed by the condensation of pyruvic acid and an alcohol having $C_1$–$C_7$ straight or branched chain alkyl hydroxy compound.

The following compounds have been found to be thromboxane synthase inhibitors in an assay method for determining the extent of thromboxane synthase inhibition. In said assay procedure, microsomes from guinea pig lung or human platelets are added to an endoperoxide intermediate in prostaglandin biosynthesis and the inhibitor in phosphate buffer solution followed by incubation, extraction and determination of the extent of thromboxane synthase inhibition by TLC with radiochromatographic profile analysis.

| | Enzyme Source* |
|---|---|
| 1-Substituted Imidazoles | |
| $IC_{50} \cong \mu M$ | |
| 4-(1H—imidazol-1-l-yl)phenol | H |
| 3-(1H—imidazol-1-ylmethyl)-1H—indole | H |
| 1-[2-(1-methylethyl)phenyl]-1H—imidazole | H |
| $IC_{50} > 1\ \mu M < 10\ \mu M$ | |
| 1-[4-(1H—imidazol-1-yl)phenyl]ethanone | G,H |
| 3-(1H—imidazol-1-yl)phenol | H |
| $IC_{50} \cong 10\ \mu M$ | |
| 1-[4-(1-methylethoxy)phenyl]-1H—imidazole | H |
| 1-(4-ethoxyphenyl)-1H—imidazole | H |
| 1-nonyl-1H—imidazole | H |
| 1-butyl-1H—imidazole | H |
| $IC_{50} > 10\ \mu M > 100\ \mu M$ | |
| 1-(triphenylmethyl)-1H—imidazole | G,H |
| 1-(phenylmethyl)-1H—imidazole | H |
| 1-(beta-0-glucopyranoxyl)-1H—imidazole | H |
| 1-[(2-chlorophenyl)diphenylmethyl]-1H—imidazole | G,H |
| 1-(4-methoxyphenyl)-1H—imidazole | H |
| 1,1'-carbonothioylbis-1H—imidazole | G |
| $IC_{50} > 100\ \mu M < 1\ mM$ | |
| 1-[2,4-dinitrophenyl]1H—imidazole | G |
| 1-(4-nitrophenyl)-1H—imidazole | G |
| 1H—imidazole | G |
| 1-[2-(2,4-dichlorophenyl)-2-[(2,4-dichlorophenyl) methoxy]-ethyl]-1H—imidazole | G |
| $IC_{50} \cong 1\ mM$ | |
| 1-acetyl-1H—imidazole | H |
| $IC_5 > 1\ mM$ | H |
| 1-ethyl-1H—imidazole | G |
| 1-[[(5-nitro-2-furanyl)methylene]amino]-2,4-imidazolidinedione | G |
| 1-methyl-1H—imidazole | G |
| 4-Substituted Imidazoles | |
| $IC_{50} > 100\ \mu M < 1\ mM$ | |
| 3-(1H—imidazole-4-yl)-2-propenoic acid methyl ester | G |
| $IC_{50} > 1\ mM$ | |
| 1H—4-nitroimidazole | G |
| 3-Substituted Pyridines | |
| $IC_{50} \cong 1\ \mu M$ | |
| [2-(1-methylethyl)-1H—indol-3-yl)]-3-pyridinyl-methanone | H |
| $IC_{50} \cong 100\ \mu M$ | |
| [(2-hydroxy-1-naphthalenyl)methylene]hydrazide 3-pyridinecarboxylic acid | H |
| $IC_{50} > 100\ \mu M < 1\ mM$ | |
| 2-methyl-1,2-di-3-pyridyl-1-propanone tartrate [1:2] | H |
| $IC_{50} > 1\ mM$ | |
| 5-amino-3-pyridinecarboxylic acid | G |
| 3-Substituted Indoles | |
| $IC_{50} \cong 1\ \mu M$ | |
| [2-(1-methylethyl)-1H—indol-3-yl)]-3-pyridinyl-methanone | H |
| 3-(1H—imidazol-1-ylmethyl)-1H—indole | H |
| $IC_{50} > 100\ \mu M < 1\ mM$ | |
| 1-(4-chlorobenzoyl)-5-methoxy-2-methyl-1H—indole-3-acetic acid | G |
| 4-Substituted Pyrimidines | |
| $IC_{50} \cong 100\ \mu M$ | |
| 4-phenylpyrimidine | G |
| $IC_{50} > 100\ \mu M < 1\ mM$ | |
| Alpha-oxo-4-pyrimidinepropanoic acid ethyl ester | H |
| [6R-(6α, 7β)]-2-carboxy-8-oxo-3-[(4-pyrimidinylthio) methyl]5-thia-1-azabicyclo-[oct-2-en-7-aminum | H |

-continued

| | Enzyme Source* |
|---|---|
| hydroxide inner salt | |
| 5-Substituted Tetrazoles | |
| $IC_{50} > 100\ \mu M < 1\ mM$ | |
| 3-(1H—tetrazol-5-yl)-9H—thioxathen-9-one s.s. dioxide | G |
| Pyrazolidines | |
| $IC_{50} \cong 1\ mM$ | |
| 1,2-diphenyl-4-[2-[phenylsulfinyl]ethyl]-3,5-pyrazolidinedione | G |
| Quinazolines | |
| $IC_{50} > 1\ mM$ | |
| 7-methyl-1-(1-methylethyl)-4-phenyl-2-(1H)—quinazolinone | G |
| Substituted Xanthene Carboxylic Acids | |
| $IC_{50} > 1\ mM$ | |
| 7-(1-methylethoxy)-9-oxo-9H—xanthene-2-carboxylic acid | G,H |

*G = Guinea Pig Lung Microsomes
H = Human Platelet Microsomes

A number of thromboxane synthase inhibitors were evaluated in vitro to determine their ability to lower insulin secretion as indicated in Table I. Some of these compounds were, in turn, evaluated for and correlated with antiobesity activity in vivo in obese Zucker rats as indicated in Table II, Table III and FIG. 1.

The preferred compounds for use in the methodology of this invention are:

1-Substituted imidazoles of Formula I wherein R is H; $R^1$ is $C_1$–$C_9$ alkyl, 3-methamindole or para substituted aryl hydroxy;

3-Substituted Pyridines of Formula II wherein $R^2$ is 3-indolo.

The most preferred compounds are:

4-(1H-imidazol-1-yl)phenol
3-(1H-imidazol-1-ylmethyl)-1H-indole
1-[4-(1H-imidazol-1-yl)phenyl]ethanone
1-[4-(1-methylethoxy)phenyl]-1H-imidazole
1-(triphenylmethyl)-1H-imidazole
1,1'-carbonothioylbis-1H-imidazole
[2-(1-methylethyl)-1H-indol-3-yl)]-3-pyridinyl-methanone The thromboxane synthase inhibitors of the present invention may be administered in the form of pharmaceutically-acceptable, nontoxic anionic salts. Preferred salts for this purpose include hydrochloride, nitrate sulfate and tartrate salts.

The thromboxane synthase inibitors of the present invention can be administered in dosages of 0.1 to 200 mg per kg per day, preferably 0.1 to 50 mg per kg per day, most preferably 0.1 to 10 mg per kg per day.

For purposes of administration, the thromboxane synthase inhibitors of the present invention can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form and may additionally contain other therapeutically-valuable substances or conventional pharmaceutical adjuvants such as preservatives, stabilizing agents, wetting agents, emulsifying agents, buffers and the like. The pharmaceutical preparations can be in conventional solid dosage forms such as tablets, capsules, dragees, and the like, conventional semi-solid forms such as ointments and creams, conventional liquid forms such as solutions, suspension, emulsions and the like and other conventional dosage forms such as dry ampules, suppositories and the like. Such preparations may be submitted to conventional pharmaceutical expedients such as, for example, sterilization and the like.

The methodology of the present invention can be better understood by reference to the following embodiments:

EXAMPLE I

Determination of Inhibition of Thromboxane Synthase Activity Isolation of Human Platelet Microsomes Platelets were obtained from 320 ml of whole blood and resuspended in 5.0 ml of Krebs-Hensleit buffer ($CA^{+2}$ free). After three consecutive freeze-thawing cycles, homogenization and centrifugation at 12,000 g for 45 min., the 12,000 g supernatant was recentrifuged at 110,000 g for 60 min. The resultant pellet was resuspended in phosphate buffer (0.5 ml, 0.1M, pH 7.5) and stored at $-70^\circ$ C. until use.

Isolation of Guinea Pig Lung Microsomes

Four male guinea pigs (≅500 g each) were sacrificed by spinal dislocation. The lungs were removed, freed of trachea and the majority of blood removed by rinsing the lungs with buffer (0.1M phosphate pH 7.5) via the pulmonary artery. The lung tissue (18.3 g total wet wt.), was then minced, suspended in three volumes of buffer and homogenized using, initially, a Brinkmann polytron homogenizer and, finally, a glass-teflon tissue grinder. The homogenate was centrifuged at 12,000 g for 1 hr. and the resultant supernatant recentrifuged at 110,000 g for 1 hr. The 110,000 g pellet was taken up in 10 ml of buffer, divided into 5×2 ml aliquots and stored at $-70^\circ$ until use.

Endoperoxide

Low specific activity $PGH_2$ (3.3 μCi/μmole) was obtained from Dr. W. E. M. Lands of the University of Michigan. $PGH_2$ of higher specific activity (16.0 μCi/μmole) was purchased from Ran Biochemicals, Tel-Aviv, Israel.

Inhibitors

The inhibitors tested were prepared as solutions (1-10 mg/ml) in 95% ethanol. The amounts of ethanol used were found to have no significant effect on the thromboxane synthase assays.

Assay for Thromboxane Synthase

To a 12×75 mm tube containing $[1-{}^{14}C]$ $PGH_2$ (2 μg, 0.01 μCi or 0.05 μCi) and inhibitor (1 mM final assay concentration, in 10 μl of ethanol) in 225 μl of phosphate buffer (0.1M, pH 7.5), was added to an aliquot of guinea pig lung mocrosomes (25 μl, containing 400 μg protein) or an aliquot of human platelet microsomes (25 μl, containing ≅130 g protein). The solution was incubated in a 22° water bath for 2 min.; ether (1 ml) and citric acid (25 μMoles) were added, and the tube plunged into an acetone-dry ice bath. The ether extract was transferred to a 1.0 ml Reacti-vial, and the volume reduced under nitrogen to ≅50 μl.

The extract was applied to an I.T.L.C., type SG, glass fiber sheet (Gelman Instrument Co., Ann Arbor, Mich.) and developed in isooctane: methyl ethyl ketone: acetic acid (100:19:1 or 100:9:1) (19). The sheets were air dried and scanned using a Berthold LB 2760 Radiochromatographic Scanner. In certain cases, based on the radiochromatographic profile obtained, the sheets were cut, the appropriate regions placed in scintillation vials, 10 ml of LSC cocktail (Yorktown Research, S. Hackensack, N.J.) added, and the relative cpm determined.

EXAMPLE 2

Determination of Insulin-Secretory Activity in the Isolated Perfused Rat Pancreas Pancreata were obtained from young adult female Charles River rats weighing from 200-300 g. The animals were anaesthesized with sodium pentobarbitol (45 mg/kg), injected intraperitoneally, and the pancreas with its intact vasculature was removed and connected to an extracorporeal perfusion apparatus.

The basic perfusion solution contained: 133 mM NaCl, 4.4 mM KCl, 2.5 mM $MgSO_4$, 2.4 mM Ca gluconate, 1.5 mM $KH_2PO_4$, 29.4 mM $NaHCO_3$, 4% dextran and 0.2% bovine serum albumin and glucose as discussed below. The perfusion flow rate was kept constant at 4 ml/min. After a 15-20 min equilibration period, the experimental protocol was begun. The pancreatic effluent was collected in either one or four-minute fractions.

The perfusion was run in the following sequence:

10 min 5.6 mM glucose
30 min 16.7 mM glucose—internal control
10 min 5.6 mM glucose
30 min 16.7 mM glucose and test compound
10 min 16.7 mM glucose
10 min 5.6 mM glucose
5 min 20 mM arginine—to check pancreas viability Test compounds were dissolved in 90% ethanol to a concentration of 25 mM and then diluted in the perfusion buffer to the desired concentration. The perfusion effluent was collected in one or four min fractions—the samples were checked immediately, aliquoted for submission to radioimmunoassay and stored at $-20^\circ$ C. until the time of assay. The radioimmunoassay of insulin was carried out by a back-titration method using a pure rat insulin standard.

To assess the inhibitory activity of the test compounds, an inhibition index was calculated. The inhibition index is derived by comparing the insulin secretion response from treated versus nontreated pancreas preparations. For each preparation, a ratio of insulin secretion was calculated from the area under the insulin secretion curve of the first pulse of 16.7 mM glucose divided by the area under the curve of the second pulse of 16.7 mM glucose containing compound.

The thromboxane synthase inhibitors of the present invention significantly reduced insulin secretion in the perfused rat pancreas.

EXAMPLE 3

Determination of Antiobesity Activity

Thromboxane synthase inhibitors were evaluated for antiobesity activity in vivo. Body weight, food intake and circulating insulin levels were monitored during periods of drug treatment. Analysis of carcass composition was performed at study termination.

Animals, Diets and Drug Administration

Lean and obese male and female Zucker rats bred at Hoffmann-La Roche Inc. (Nutley, N.J.) were kept in wire-bottomed individual cages in light (12 hr dark and light cycles beginning at 6 p.m. and 6 a.m., respectively) and temperature-controlled (22°) rooms. All rats were fed chow diet (Ralston Purina Co., St. Louis, Mo.) ad libitum until one to three weeks before the start of drug treatment, at which time they were trained to consume a high glucose low fat (1% corn oil) diet which is herein referred to as G-70:1% CO. Following the one to three-week training period on G-70:1% CO, the average daily food intake was calculated, and the rats were weighed and divided into groups of four to seven rats each.

The control animals continued to eat the G-70:1% CO diet ad libitum, and the experimental groups were given G-70:1% CO diet containing drug (also fed ad libitum). The amount of drug added to the diet of each experimental group was based on calculations of food consumed per kg body weight using data collected at the end of the training period. The age of the rats at the start of drug treatment was between two to five months but, within each study age, did not vary more than three weeks. The period of drug treatment ranged from 16 to 18 days as noted in the legends to the tables and graph. Food intake and body weight were recorded either daily or twice a week throughout the duration of the study. The amount of drug administered was calculated from the food intake per kg body weight for each experimental group. Body weight data are reported as the difference between the body weight gains of control and drug-treated animals. Food intake and insulin data are reported as percent of control.

In one study, carcass composition was determined. After treatment, rats were sacrificed by decapitation, and livers and blood were removed. Carcasses were weighed, saponified in alcoholic potassium hydroxide, acidified and extracted with petroleum ether. The petroleum ether supernatants were transferred to preweighed glass vials, evaporated immediately to dryness under nitrogen and reweighed. Total carcass data are expressed in grams and percentages of carcass weight. An aliquot of saponified carcass extract was neutralized, and total carcass nitrogen was determined using Kjeldahl procedure. Carcass protein data are expressed in grams and percentages of carcass weight.

The thromboxane synthase inhibitors of the present invention significantly reduced body weight gain in obese Zucker rats (Table II and FIG. 1). Body weight loss was maintained throughout the treatment period in the drug-treated groups. This reduction in body weight was achieved by a significant lowering of body fat (Table III). As desired, body protein levels remained unchanged.

TABLE I

EFFECT OF THROMBOXANE SYNTHASE INHIBITORS ON INSULIN SECRETION BY ISOLATED PERFUSED RAT PANCREAS

| Class | Compound | $TXA_2$ Synthase $IC_{50}$ μM | Insulin Secretion Concentration μM | Insulin Secretion Inhibition Index[a] |
|---|---|---|---|---|
| Control | | | | 1.0 ± 0.04 (n = 5) |
| 1-substituted-imidazole | imidazole | 600 | 100 | 2 |
| | | | 1000 | 3 |
| | 1-(triphenylmethyl)-1H—imidazole | 10–100 | 10 | 2 |
| | 1-[4-1H—imidazol-1-yl)phenyl]ethanone | 10 | 100 | 2 |
| | 4-(1H—imidazol-1-yl)phenol | 1 | 10 | 2 |
| | 3-(1H—imidazol-1-ylmethyl)-1H—indole | 1 | 10 | 1 |
| | | | 50 | 13 |
| | | | 100 | 32 |
| | 1-[4-(1-methylethoxy)phenyl]-1H—imidazole | 10 | 100 | 4 |
| | 1,1'-carbonothioylbis-1H—imidazole | 15 | 1000 | 5 |
| 3-substituted-pyridine | [2-(1-methylethyl)-1H—indol-3-yl)]-3-pyridinyl-methanone | 1 | 100 | 5 |

TABLE II

ANTIOBESITY ACTIVITY OF THROMBOXANE SYNTHASE INHIBITORS IN OBESE ZUCKER RATS

| Class | Compound | Dose[a] mg/kg | Body Weight Gain[b] g | Food Consumption % of control | Insulin % of control |
|---|---|---|---|---|---|
| Control | | | | 100 ± 3 | 100 ± 15 |
| 1-substituted-imidazole | 1-[4-(1H—imidazol-1-yl)phenyl]ethanone | 60 | −25* | 82 ± 3* | 66 ± 16 |
| | | 87 | −32* | 84 ± 1* | 32 ± 5* |
| | | 113 | −74* | 74 ± 1* | 24 ± 1* |
| | 3-(1H—imidazol-1-ylmethyl)-1H—indole | 18 | −24* | 81 ± 1* | 72 ± 9* |
| | | 55 | −68* | 63 ± 4* | 12 ± 2* |
| | 1-[4-(1-methylethoxy)phenyl]1H—imidazole | 82 | −18* | 80 ± 2* | 94 ± 21 |
| 3-substituted-pyridine | [2-(1-methylethyl)-1H—indol-3-yl)]-3-pyridinyl-methanone | 94 | −17* | 89 ± 4 | |

[a]Average duration of treatment was 16 to 18 days.
[b]Body weight gain was computed by taking the difference between the weight gain of treated and control rats.
*Significantly different from control ($P \leq 0.05$).

TABLE III

EFFECT OF 1-[4-(1H—IMIDAZOL-1-YL)PHENYL]ETHANONE ON CARCASS WEIGHT AND CAARCASS LIPID AND PROTEIN LEVELS IN MALE ZUCKER RATS[a]

| Treatment | Genotype | Carcass Weight g | Carcass Lipids total (g) | Carcass Lipids % of carcass weight | Carcass Protein total (g) | Carcass Protein % of carcass weight |
|---|---|---|---|---|---|---|
| Control | Lean | 428 ± 9 | 57 ± 2 | 13 ± 0 | 81 ± 6 | 19 ± 1 |

TABLE III-continued

EFFECT OF 1-[4-(1H—IMIDAZOL-1-YL)PHENYL]ETHANONE ON CARCASS WEIGHT AND CAARCASS LIPID AND PROTEIN LEVELS IN MALE ZUCKER RATS[a]

| Treatment | Genotype | Carcass Weight g | Carcass Lipids total (g) | Carcass Lipids % of carcass weight | Carcass Protein total (g) | Carcass Protein % of carcass weight |
|---|---|---|---|---|---|---|
| | | (100)[c] | (100) | (100) | (100) | (100) |
| 1-[4-(1H—imidazol-1-yl)phenyl]ethanone (98 mg)[b] | Lean | 361 ± 27* (84) | 29 ± 5* (50) | 8 ± 1* (60) | 75 ± 5 (87) | 21 ± 2 (111) |
| Control | Obese | 556 ± 22 (100) | 263 ± 13 (100) | 47 ± 1 (100) | 74 ± 3 (100) | 13 ± 1 (100) |
| 1-[4-(1H—imidazol-1-yl)phenyl]ethanone (87 mg)[b] | Obese | 460 ± 28* (83) | 225 ± 6 (86) | 49 ± 1 (104) | 81 ± 4 (109) | 18 ± 2 (131) |

[a]Four month old male Zucker rats (four per group) were fed G-70:1% corn oil diet ad libitum for 24 days prior to treatment. 1-[4-(1H—imidazol-1-yl)phenyl]ethanone was then mixed into the G-70:1% corn oil diet and rats were fed ad libitum for 29 days. On day 29 rats were killed by decapitation and the carcasses (minus liver and blood) were analyzed for total lipid and protein. Each value is the mean ± S.E.

[b]Amount of 1-[4-(1H—imidazol-1-yl)phenyl]ethanone ingested per day per kg body weight.

[c]Values in parentheses indicate percent of control.

*$P \leq 0.05$.

What is claimed is:

1. A method for reducing body weight in obese mammals which comprises orally administering, to the mammal to be treated, an amount effective for reducing body weight of a thromboxane synthase inhibitor of the formula:

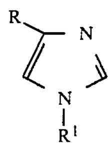

FORMULA I wherein R is H, $NO_2$, or $—C_2–C_4$ alkenyl; $R^1$ is H, $C_1–C_{11}$ alkyl, acetyl, propionyl, butyryl, phenyl, phenyl substituted by one or two substituents independently selected from the group consisting of $C_1–C_3$ alkoxy, $C_1–C_4$ alkyl, Cl, F, Br, $NO_2$, acetyl, propionyl, butyryl or hydroxy, phenylalkyl, or 3-indolo optionally substituted at the two position by $C_1–C_4$ straight or branched chain alkyl.

2. The method of claim 1 wherein R is H, $R^1$ is $C_1–C_9$ alkyl or para substituted phenyl hydroxy.

3. The method of claim 1 wherein said thromboxane synthase inhibitor is 4-(1H-imidazol-1-yl)phenol.

4. The method of claim 1 wherein said thromboxane synthase inhibitor is 3-(1H-imidazol-1-ylmethyl)-1H-indole.

5. The method of claim 1 wherein said thromboxane synthase inhibitor is 1-[2-(1-methylethyl)phenyl]-1H-imidazole.

6. The method of claim 1 wherein said thromboxane synthase inhibitor is 1-[4-(1H-imidazol-1-yl)phenyl]ethanone.

7. The method of claim 1 wherein said thromboxane synthase inhibitor is 3-(1H-imidazol-1-yl)phenol.

8. The method of claim 1 wherein said thromboxane synthase inhibitor is 1-[4-(1-methylethoxy)phenyl]-1H-imidazole.

9. The method of claim 1 wherein said thromboxane synthase inhibitor is 1-(4-ethoxyphenyl)-1H-imidazole.

10. The method of claim 1 wherein said thromboxane synthase inhibitor is 1-nonyl-1H-imidazole.

11. The method of claim 1 wherein said thromboxane synthase inhibitor is 1-butyl-1H-imidazole.

12. The method of claim 1 wherein said thromboxane synthase inhibitor is 1-(triphenylmethyl)-1H-imidazole.

13. The method of claim 1 wherein said thromboxane synthase inhibitor is 1-(phenylmethyl)-1H-imidazole.

14. The method of claim 1 wherein said thromboxane synthase inhibitor is 1-(beta-D-glucopyranosyl)-1H-imidazole.

15. The method of claim 1 wherein said thromboxane synthase inhibitor is 1-[(2-chlorophenyl)diphenylmethyl]-1H-imidazole.

16. The method of claim 1 wherein said thromboxane synthase inhibitor is 1-(4-methoxyphenyl)-1H-imidazole.

17. The method of claim 1 wherein said thromboxane synthase inhibitor is 1,1′-carbonothioylbis-1H-imidazole.

18. The method of claim 1 wherein said thromboxane synthase inhibitor is 1-[2,4-dinitrophenyl]1H-imidazole.

19. The method of claim 1 wherein said thromboxane synthase inhibitor is 1-(4-nitrophenyl)-1H-imidazole.

20. The method of claim 1 wherein said thromboxane synthase inhibitor is 1H-imidazole.

21. The method of claim 1 wherein said thromboxane synthase inhibitor is 1-[2-(2,4-dichlorophenyl)-2-[(2,4-dichlorophenyl)methoxy]ethyl]-1H-imidazole.

22. The method of claim 1 wherein said thromboxane synthase inhibitor is 1-acetyl-1H-imidazole.

23. The method of claim 1 wherein said thromboxane synthase inhibitor is 1-ethyl-1H-imidazole.

24. The method of claim 1 wherein said thromboxane synthase inhibitor is 1-[[(5-nitro-2-furanyl)methylene]amino]-2,4-imidazolidinedione.

25. The method of claim 1 wherein said thromboxane synthase inhibitor is 1-methyl-1H-imidazole.

26. The method of claim 1 wherein said thromboxane synthase inhibitor is 3-(1H-imidazol-4-yl)-2-propenoic acid methyl ester.

27. The method of claim 1 wherein said thromboxane synthase inhibitor is 1H-4-nitroimidazole.

28. The method of claim 1 wherein said thromboxane synthase inhibitor is administered in dosages ranging from 0.1–200 mg per kg per day.

29. The method of claim 1 wherein said thromboxane synthase inhibitor is administered in dosages ranging from 0.1–50 mg per kg per day.

30. The method of claim 1 wherein said thromboxane synthase inhibitor is administered in dosages ranging from 0–10 mg per kg per day.

31. An oral composition for reducing body weight in obese mammals which comprises a pharmaceutically-acceptable carrier material and an amount effective for reducing body weight of a compound of the formula:

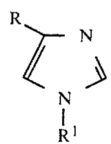

FORMULA I wherein

R is H, $NO_2$, or $C_2$–$C_4$ alkenyl;

$R^1$ is H, acetyl, propionyl, butyryl, phenyl, phenyl substituted by one or two substituents independently selected from the group consisting of $C_1$–$C_3$ alkoxy, $C_1$–$C_4$ alkyl, Cl, F, Br, $NO_2$, acetyl, propionyl, butyryl, or hydroxy, or 3-indolo optionally substituted at the two position by $C_1$–$C_4$ straight or branched chain alkyl.

32. A composition in accordance with claim 31, wherein the compound of formula I is 1-[4-(1H-imidazol-1-yl)phenyl]ethanone.

33. A composition in accordance with claim 31, wherein the compound of formula I is 3-(1H-imidazol-1-ylmethyl)-1H-indole.

* * * * *